Oct. 9, 1945. E. PRUSHEK Plant Pat. 660
CHRYSANTHEMUM PLANT
Filed Nov. 30, 1944
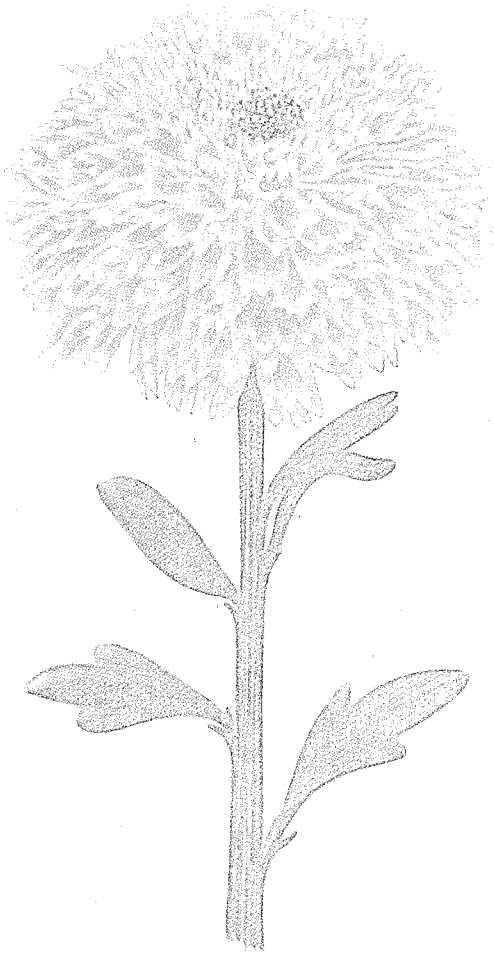
INVENTOR.
Emil Prushek
BY Robb & Robb
His attorneys Patented Oct. 9, 1945

Plant Pat. 660

UNITED STATES PATENT OFFICE

660

CHRYSANTHEMUM PLANT

Emil Prushek, Benton Harbor, Mich., assignor to R. M. Kellogg Co., Three Rivers, Mich., a corporation of Michigan Application November 30, 1944, Serial No. 565,881

1 Claim. (Cl. 47—60)

The present invention relates to a new and distinct variety of chrysanthemum plant, of that type most generally known as "Azaleamum."

This new variety was originated by me by crossing of the variety "Glomero" with an unnamed seedling and its outstanding feature of novelty resides in the form of the flower, particularly the shape of its petals which imparts to the flower, the appearance of or resemblance to a carnation. That is to say, the flower petals are characteristically notched or serrated at their tips, nearly every petal having one rather deep notch, usually at the center, and one smaller notch usually to the right of the center notch, but sometimes to the left.

This new chrysanthemum is further characterized as to novelty by the changes of color of its flowers during their stages of development, running from Deep Hellebore, as the buds begin to open, then to Daphne Red, tipped with white, as the flowers freshly open, and finally to a predominating color of Tyrian Pink with more pronounced white tips of the petals, and Laelia Pink on reverse of petals. This mutation of coloring of the petals and form thereof above mentioned lend great attraction to this new variety, imparting to the flower a rose-like appearance.

Other features of novelty which enhance the value of this variety are as follows: The plant itself is thrifty and a vigorous grower. For example, one year old plants will attain an average size of eighteen inches high and twenty-five inches in diameter under good conditions with a larger growth as its age increases and it grows to a characteristically symmetrical mound shape that is very compact. Relatively speaking, however, it is classed as small in size, or dwarfish.

The foliage of the plant is very healthy and attractive and from observation has shown a marked resistance to chrysanthemum leaf spot. At the same time, the plant is definitely hardy.

Asexual reproduction of this plant, by means of a moderate number of strong sprouts around its base, shows the foregoing characteristics to be established.

The following is a detailed description of this new chrysanthemum, the color terminology employed herein being in accord with that of Ridgway's Color Standard, except where obviously the meaning is in the sense of the popular or dictionary color term.

Parentage: Seedling.
- *Seed parent.*—Unnamed variety.
- *Pollen parent.*—"Glomero."

Classification:
- *Botanical.*—*Chrysanthemum hortorum.*

*Flower*

Blooming habit: Blooms early and profusely. Recurrent—continuous in fall.

Bud:
- *Size.*—Medium. Is not affected by wet or hot weather.
- *Color.*—As buds open the petals are Deep Hellebore Red, Plate XXXVIII 71''*i*.

Bloom: Average size when fully expanded, 1¾ inches.
- *Borne.*—Singly.
- *Stems.*—Medium length; strong.
- *Petalage.*—Very double (many petals and stamens hidden), averaging 12 rows of petals. Number of petals under normal conditions—approximately 150.
- *Color.*—Freshly opened flowers are predominately Daphne Red, Plate XXXVIII 69''–. Petals are tipped with white. After opening, flowers change to a predominating color of Tyrian Pink, Plate XII 69*b*, and white tips are more pronounced. Reverse of petals is Laelia Pink, Plate XXXVIII 67''*d*.

Petals:
- *Appearance.*—Inside and outside—satiny.
- *Petaloids in center.*—None.
- *Persistence.*—Hang on.
- *Fragrance.*—Strong; chrysanthemum odor.
- *Lasting quality.*—On the plant and as cut flower—very long.

Genital organs:
- *Stamens, anthers.*—Medium size; many. Color—yellow.
- *Stamens, filaments (threads).*—Short. Color—lemon yellow.
- *Pollen.*—Gold yellow.
- *Styles.* — Columnar; bunched; medium length; heavy.
- *Stigmas.*—All enclosed in calyx.

Fruit: Variety is sterile with its own pollen.

*Plant*

Form: Compact round topped bush.

Growth: Vigorous; dwarf; branching; compact.

Foliage:
- *Size.*—Small leaflets.
- *Quantity.*—Abundant.
- *Color.* — New foliage: Upper side—Cerro Green, Plate V 25*m*; under side—Biscay Green, Plate XVII 25'*i*. Old foliage: upper side—Dark Dull Yellow Green, Plate XXXII 31''*m*; under side—Light Hellebore Green, Plate XVII 25'K.
- *Shape.*—Ternate.

*Texture.*—Under side—very slight pubescence. Ribs and veins—ordinary.

*Edge.*—Sinuate.

*Serration.*—Single; deep; with single shallow notch at side.

*Leaf stem.*—Green. Under side—slightly pubescent.

*Stipules.*—Short; serrated.

*Disease resistance.*—Resistant to crysanthemum leaf spot.

Wood:

*New wood.*—Light green. Bark—smooth.

*Old wood.*—Greenish brown. Bark—smooth.

I claim:

A new and distinct variety of chrysanthemum plant, characterized as to novelty by the peculiarly notched form of the flower petals, giving to the blooms the appearance of a carnation; the coloring of the flowers during the different development stages; the thrifty, vigorous growth and hardiness of the plant, in combination with its mound shape; and its marked resistance to chrysanthemum leaf spot, substantially as shown and described.

EMIL PRUSHEK.